United States Patent
Morrissey et al.

(10) Patent No.: US 10,828,158 B2
(45) Date of Patent: Nov. 10, 2020

(54) CATHETER SHAFT CONSTRUCTION FOR TAVR DELIVERY SYSTEMS

(71) Applicant: St. Jude Medical, Cardiology Division, Inc., St. Paul, MN (US)

(72) Inventors: Michael Shane Morrissey, St. Paul, MN (US); Sadie J. Cronin, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 205 days.

(21) Appl. No.: 16/143,836

(22) Filed: Sep. 27, 2018

(65) Prior Publication Data

US 2019/0099270 A1    Apr. 4, 2019

Related U.S. Application Data

(60) Provisional application No. 62/565,661, filed on Sep. 29, 2017.

(51) Int. Cl.
| | |
|---|---|
| *A61F 2/24* | (2006.01) |
| *A61B 17/00* | (2006.01) |
| *A61F 2/966* | (2013.01) |
| *A61F 2/95* | (2013.01) |

(52) U.S. Cl.
CPC ...... *A61F 2/2436* (2013.01); *A61B 17/00234* (2013.01); *A61B 2017/00243* (2013.01); *A61F 2/9517* (2020.05); *A61F 2/966* (2013.01)

(58) Field of Classification Search
CPC .......... A61F 2/95; A61F 2/9517; A61F 2/966; A61F 2/962; A61F 2/9522; A61F 2/2436; A61F 2002/9623; A61F 2002/9528; A61F 2002/9534; A61B 17/00234; A61B 2017/00243

See application file for complete search history.

(56) References Cited

U.S. PATENT DOCUMENTS

| | | | |
|---|---|---|---|
| 6,786,918 B1 * | 9/2004 | Krivoruchko | A61F 2/95 623/1.11 |
| 7,771,369 B2 * | 8/2010 | Griffin | A61M 25/01 600/434 |
| 2002/0095203 A1 * | 7/2002 | Thompson | A61F 2/95 623/1.11 |
| 2013/0297011 A1 * | 11/2013 | Morris | A61F 2/2436 623/2.11 |

\* cited by examiner

*Primary Examiner* — Ashley L Fishback
(74) *Attorney, Agent, or Firm* — Lerner, David, Littenberg, Krumholz & Mentlik, LLP

(57) ABSTRACT

A delivery device for a collapsible prosthetic heart valve may include an operating handle having a housing and a carriage movable relative to the housing, and a catheter assembly. The catheter assembly may have an inner shaft around which a compartment is defined, an outer shaft surrounding at least a portion of the inner shaft, a distal sheath fixedly connected to the outer shaft, and a spline tube surrounding at least a portion of the inner shaft. The spline tube may have thinner portions having a first maximum thickness in a radial direction of the inner shaft and thicker portions having a second maximum thickness in the radial direction that is greater than the first maximum thickness. The spline tube and the outer shaft may together define one or more channels that provide liquid communication between the operating handle and the compartment.

17 Claims, 2 Drawing Sheets

CATHETER SHAFT CONSTRUCTION FOR TAVR DELIVERY SYSTEMS

CROSS-REFERENCE TO RELATED APPLICATIONS

This application claims the benefit of the filing date of U.S. Provisional Patent Application No. 62/565,661, filed on Sep. 29, 2017, the disclosure of which is hereby incorporated herein by reference.

BACKGROUND OF THE INVENTION

The present invention is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheathes the annulus end of the valve, so that the valve can be repositioned while in a collapsed state. After the valve has been repositioned, the user can again release the valve.

Once a self-expanding valve has been fully deployed, it expands to a diameter larger than that of the sheath that previously contained the valve in the collapsed condition, making resheathing impossible, or difficult at best. In order for the user to be able to resheathe a partially-deployed valve, a portion of the valve must still be collapsed inside of the sheath.

Despite the various improvements that have been made to the collapsible prosthetic heart valve delivery process, conventional delivery devices, systems, and methods suffer from some shortcomings. For example, in conventional delivery devices for self-expanding valves, it is difficult to completely resheathe the valve after partial deployment, due to axial compression of the distal sheath during the resheathing process and/or axial stretch or compression of the inner and/or outer shafts of the delivery device.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

BRIEF SUMMARY OF THE INVENTION

Described herein is a delivery device for a collapsible prosthetic heart valve. The delivery device may include a catheter assembly and an operating handle. The operating handle may be coupled to the catheter assembly. The operating handle may have a housing and a carriage movable relative to the housing. The catheter assembly may include an inner shaft around which a compartment is defined, an outer shaft surrounding at least a portion of the inner shaft, a distal sheath fixedly connected to the outer shaft, and a spline tube surrounding at least a portion of the inner shaft. The inner shaft being operatively connected to the housing. The compartment may be adapted to receive the valve in an assembled condition. The outer shaft may be fixedly connected to the carriage and movable relative to the inner shaft and the housing. The outer shaft may define a lumen therein having an inner surface.

The distal sheath may be movable between a closed condition covering the compartment and an open condition uncovering the compartment for deployment of the valve. At least a portion of the spline tube may be disposed in the lumen of the outer shaft. The spline tube may have first portions with a first maximum thickness in a radial direction of the inner shaft and second portions with a second maximum thickness in the radial direction, the second maximum thickness being greater than the first maximum thickness. The spline tube and the outer shaft may together define one or more channels each at least partially bounded by the inner surface of the outer shaft, one of the first portions, and two adjacent ones of the second portions. The one or more channels may provide liquid communication between the operating handle and the compartment.

Also described herein is a method of flushing a liquid into a compartment of a delivery device for implanting a medical device in a patient. The method may include providing the delivery device having a catheter assembly and an operating handle. The operating handle may include a housing and a carriage movable relative to the housing. The catheter assembly may include an inner shaft around which a compartment for the medical device is defined, an outer shaft surrounding at least a portion of the inner shaft, a distal sheath fixedly connected to the outer shaft, and a spline tube surrounding at least a portion of the inner shaft. The distal sheath may be movable between a fully closed condition covering the compartment and an open condition uncovering the compartment.

At least a portion of the spline tube may be disposed in the lumen of the outer shaft. The spline tube and the outer shaft may together define one or more channels providing liquid communication between the operating handle and the compartment. The method may also include mounting the medical device in the compartment, sliding the distal sheath to cover the compartment and the medical device, and flushing the liquid from the operating handle to the compartment through the one or more channels. The spline tube may have first portions having a first maximum thickness in a radial direction of the inner shaft and second portions having a second maximum thickness in the radial direction, the second maximum thickness being greater than the first maximum thickness. The one or more channels each may be at least partially bounded by the inner surface of the outer shaft, one of the first portions, and two adjacent ones of the second portions.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, the terms "proximal" and "distal" are to be taken as relative to a user using the disclosed delivery devices. "Proximal" is to be understood as relatively close to the user and "distal" is to be understood as relatively farther away from the user. As used herein, the terms "generally," "substantially," "approximately," and "about" are intended to mean that slight deviations from absolute are included within the scope of the term so modified.

Figure 1A:
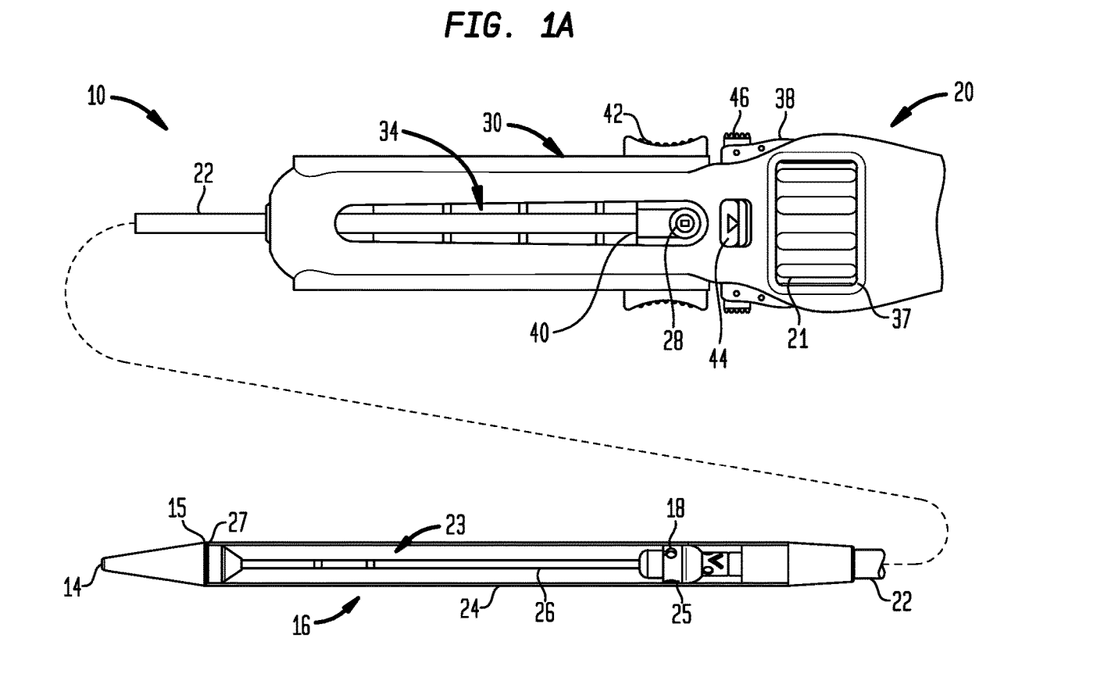
FIG. 1A is a top plan view of a portion of an operating handle of a transfemoral delivery device for a collapsible prosthetic heart valve, shown with a partial longitudinal cross-section of the distal portion of a transfemoral catheter assembly.
Figure 1B:
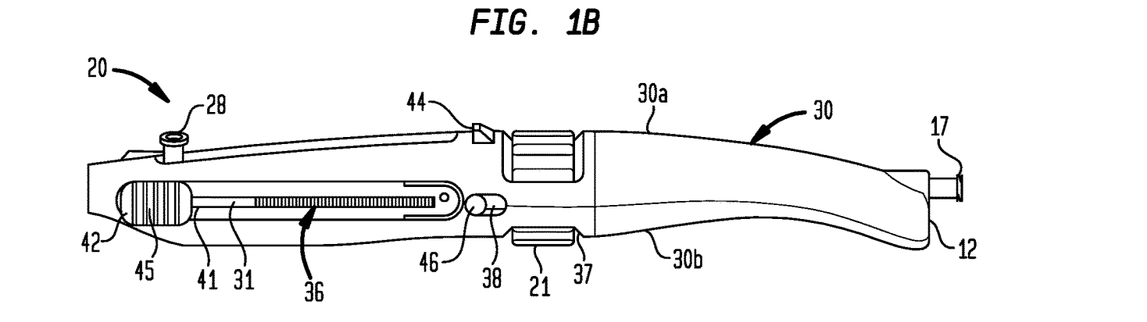
FIG. 1B is a side view of the handle of FIG. 1A.
Figure 1C:
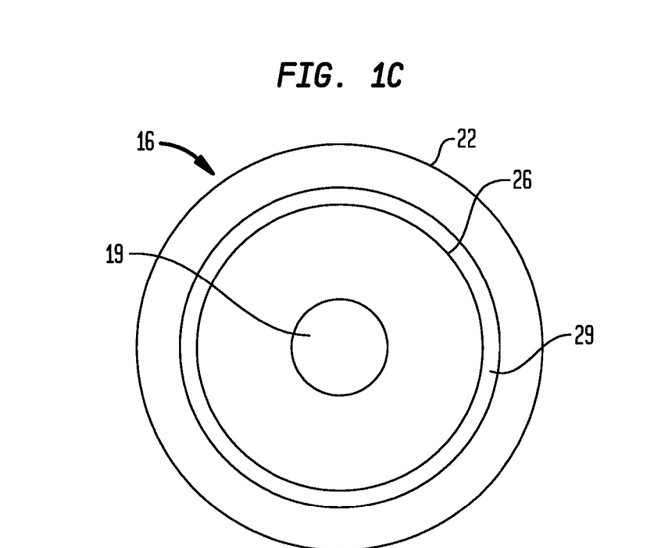
FIG. 1C is a lateral cross-section through a catheter assembly suitable for use with the delivery device of FIG. 1A, according to one embodiment.

Referring now to FIGS. 1A-1C to illustrate the structure and function of the present invention, an exemplary transfemoral delivery device 10 for a collapsible prosthetic heart valve (or other types of implantable medical devices) has a catheter assembly 16 for delivering the heart valve to and deploying the heart valve at a target location, and an operating handle 20 for controlling deployment of the valve from the catheter assembly. The delivery device 10 extends from a proximal end 12 (FIG. 1B) to an atraumatic tip 14 at the distal end of catheter assembly 16. The catheter assembly 16 is adapted to receive a collapsible prosthetic heart valve (not shown) in a compartment 23 defined around an inner shaft 26 and covered by a distal sheath 24.

The inner shaft 26 may extend through the operating handle 20 and the catheter assembly 16 to the atraumatic tip 14 of the delivery device, and includes a retainer 25 affixed thereto at a spaced distance from the atraumatic tip 14 and adapted to hold a collapsible prosthetic valve in the compartment 23. The inner shaft 26 may comprise or may consist essentially of a flexible material such as braided or extruded polyimide, polybutylene terephthalate (PBT), or polyetheretherketone (PEEK), for example. Using a material such as PEEK may improve the resistance of the inner shaft 26 to kinking while the catheter assembly 16 is tracking through the vasculature of a patient. The retainer 25 may have recesses 18 therein that are adapted to hold corresponding retention members of the prosthetic valve.

The inner shaft 26 has a lumen 19 (FIG. 1C) for receiving a guide wire (not shown) therethrough. The inner shaft 26 may optionally be connected to a hub that includes a luer lock coupling 17, e.g., as shown in FIG. 1B. It may be desirable to flush the inner shaft 26 with a flushing liquid such as saline in order to remove air from the lumen 19, and/or to provide lubrication for a guide wire that may be inserted through the lumen during initial loading of the delivery device 10 onto the guide wire outside of a patient.

The distal sheath 24 surrounds the inner shaft 26 and is slidable relative to the inner shaft such that it can selectively cover or uncover the compartment 23. The distal sheath 24 is affixed at its proximal end to an outer shaft 22, the proximal end of which is connected to the operating handle 20 in a manner to be described. The distal end 27 of the distal sheath 24 abuts a proximally-facing abutment surface 15 of the atraumatic tip 14 when the distal sheath is fully covering the compartment 23, and is spaced apart from the abutment surface when the compartment is at least partially uncovered.

A hemostasis valve 28 (FIG. 1B) includes an internal gasket adapted to create a seal between the inner shaft 26 and the proximal end of the outer shaft 22. The hemostasis valve 28 is in fluid communication with the compartment 23 via the space 29 (FIG. 1C) between the inner shaft 26 and the outer shaft 22. The compartment 23 and the space 29 are adapted to be flushed by inserting a flushing liquid such as saline into the hemostasis valve 28, although any other appropriate liquid may be used. It is desirable to flush the compartment 23 in order to de-air (i.e., remove air pockets or air bubbles) the area in and around a collapsible prosthetic heart valve enclosed in the compartment.

To flush the catheter assembly 16, the user may apply a pressurized flushing liquid to the hemostasis valve 28. A proximal-to-distal pressure gradient in the space 29 between the inner shaft 26 and the outer shaft 22 causes the flushing liquid to travel distally through the space. The flushing liquid may travel around the outer perimeter of the retainer 25 and into the compartment 23, which may be partially closed. While the flushing liquid is traveling distally within the compartment 23, a portion of the flushing liquid flows through the collapsible prosthetic heart valve enclosed in the compartment, thereby pushing entrapped air bubbles out of the prosthetic valve.

The operating handle 20 is adapted to control the deployment of a prosthetic valve located in the compartment 23 by permitting a user to selectively slide the outer shaft 22 proximally or distally relative to the inner shaft 26, thereby respectively uncovering or covering the compartment with the distal sheath 24. The outer shaft 22 may be made of a flexible material such as nylon 11 or nylon 12, and it may have a round braid construction (i.e., round cross-section fibers braided together) or flat braid construction (i.e., rectangular cross-section fibers braided together), for example.

The proximal end of the inner shaft 26 may be connected in substantially fixed relationship to an outer housing 30 of the operating handle 20 (the longitudinal position of the inner shaft relative to the housing may be movable in some embodiments, for example, as shown and described in the co-owned and co-pending U.S. Patent Application Pub. No. 2016/0220369, the disclosure of which is hereby incorporated by reference herein), and the proximal end of the outer shaft 22 may be affixed to a carriage assembly 40 that is slidable along a longitudinal axis of the handle housing, such that a user can selectively slide the outer shaft relative to the inner shaft by sliding the carriage assembly relative to the housing.

The handle housing 30 defines an elongated space 34 in which the carriage assembly 40 may travel. The elongated space 34 preferably permits the carriage assembly 40 to travel a distance that is at least as long as the anticipated length of the prosthetic valve to be delivered (e.g., at least about 50 mm), such that the distal sheath 24 can be fully retracted from around the prosthetic valve. A pair of slots 31 may be formed on opposite sides of the housing 30, contiguous with the elongated space 34. The length of the slots 31, minus the width of the carriage grip shafts (not shown), determines the maximum distance that the carriage assembly 40 can travel within the space 34.

The carriage assembly 40 has a body portion 41 with a threaded rod 36 extending proximally therefrom along the longitudinal axis of the housing 30. The housing 30 defines an elongated bore (not shown) that is sized to freely and slidingly receive the threaded rod 36. The elongated bore has an inner diameter slightly larger than the outer diameter of the threaded rod 36. The threaded rod 36 preferably is longer than the anticipated maximum travel distance of the carriage assembly 40 within the elongated space 34 (e.g., at least about 50 mm), such that the threaded rod 36 does not fully disengage from the deployment actuator 21 (described below) during sheathing or resheathing of the prosthetic valve.

The carriage assembly 40 further includes a pair of carriage grips 42 each attached to the body portion 41 by a respective carriage grip shaft (not shown). Although the carriage assembly 40 is shown in FIG. 1A as having two carriage grips 42, that need not be the case, and the carriage assembly may have only a single carriage grip. As shown in FIG. 1B, the lateral sides of the carriage grips 42 may include a plurality of parallel ridges 45 to facilitate grasping and moving of the carriage grips.

The handle housing 30 further defines a pocket 37 that extends through the top portion 30a and bottom portion 30b for receiving the deployment actuator 21. The deployment actuator 21 is internally threaded for selective engagement with the threaded rod 36. The pocket 37 is sized and shaped to receive the deployment actuator 21 with minimal clearance, such that the location of the deployment actuator remains substantially fixed relative to the housing 30 as it is rotated about the threaded rod 36. That is, when the deployment actuator 21 is in threaded engagement with the threaded rod 36, rotation of the deployment actuator in one direction (either clockwise or counterclockwise depending on the orientation of the threads on the threaded rod) causes the threaded rod to move proximally within the elongated bore, at the same time pulling the body portion 41 of the carriage assembly 40 proximally through the elongated space 34. Similarly, when the deployment actuator 21 is in threaded engagement with the threaded rod 36, rotation of the deployment actuator in the opposite direction causes the threaded rod to move distally within the elongated bore, at the same time pushing the body portion 41 of the carriage assembly 40 distally through the elongated space 34.

The deployment actuator 21 may be selectively placed in threaded engagement with the threaded rod 36 by a coupling assembly (not shown). A pair of buttons 46 positioned on opposite lateral sides of the coupling assembly may be slidably received in longitudinal openings 38 formed on opposite lateral sides of the housing 30. Actuation of the buttons 46 causes a split nut (not shown) to engage or disengage from the threaded rod 36, thereby selectively coupling the deployment actuator 21 to or decoupling the deployment actuator from the threaded rod. For example, when the buttons 46 are in a proximal position within the longitudinal openings 38, the split nut is in engagement with the threaded rod 36 and rotation of the deployment actuator 21 translates the threaded rod. When the buttons 46 are in a distal position within the longitudinal openings, the split nut is no longer engaged with the threaded rod 36 and the threaded rod may be translated without rotation of the deployment actuator 21 by a user grasping and moving the carriage grips 42.

The handle 20 may also include a resheathing lock adapted to limit the longitudinal movement of the carriage assembly 40 proximally within the handle housing 30, thereby preventing the user from completing the deployment of a prosthetic valve unintentionally. The initial distance that the carriage assembly 40 can travel before being limited by the resheathing lock may depend on the structure of the particular prosthetic valve to be deployed. Preferably, the initial travel distance of the carriage assembly 40 is about 3 mm to about 5 mm less than the collapsed valve length. Alternatively, the initial travel distance of the carriage assembly 40 may be about 40 mm to about 45 mm, which is about 80% to about 90% of the collapsed length of an exemplary 50 mm valve. The initial distance that the carriage assembly 40 can travel may be determined as a percentage of the collapsed length of the prosthetic valve and/or the compartment 23, including, for example, 50%, 60%, 70%, 75%, 85%, or 95%.

Further details of the coupling assembly and embodiments of resheathing locks suitable for use with the delivery device 10 are shown and described in co-pending and co-owned U.S. Patent Application Pub. No. 2013/0297011, the disclosure of which is hereby incorporated by reference herein.

The operation of the delivery device 10 of FIGS. 1A-1C to deploy a prosthetic valve will now be described. To load the delivery device 10 with a collapsible prosthetic valve, the user may place the buttons 46 in the distalmost position within the openings 38 to disengage the deployment actuator 21 from the threaded rod 36. The carriage grips 42 may then be slid proximally relative to the slots 31 to move the carriage assembly 40 proximally and thereby retract the distal sheath 24 and expose the compartment 23. A compressed or crimped valve may then be loaded around the inner shaft 26, and the proximal end of the valve may be coupled to the retainer 25. The carriage grips 42 may then be slid in the opposite or distal direction relative to the slots 31 to move the carriage assembly 40 distally and cover the compartment 23 with the distal sheath 24 to hold the valve in the collapsed state.

The buttons 46 may then be placed in the starting condition of the delivery device 10. In this starting condition, the handle 20 will be in an initial state with the carriage assembly 40 at its distalmost position within the handle housing 30, and the buttons 46 will each be at the proximal most position within the respective openings 38, such that the deployment actuator 21 is threadedly engaged with the threaded rod 36.

To use the operating handle 20 to deploy a prosthetic valve that has been loaded into the compartment 23 and covered by the distal sheath 24, the user may rotate the deployment actuator 21, causing the carriage assembly 40 to translate proximally within the elongated space 34 in the housing 30. Because the distal sheath 24 is affixed to the outer shaft 22, which in turn is affixed to the carriage assembly 40, and because the inner shaft 26 is fixed to the housing 30, sliding the carriage assembly proximally relative to the housing will retract the distal sheath proximally from the compartment 23, thereby exposing and initiating deployment of the valve located therein.

The engagement of the resheathing lock may prevent full deployment of the valve beyond the predetermined percentage of the collapsed length of the valve, for example, 80%. When the deployment procedure has reached a partial deployment of the valve, for example, deployment of about 80% of the length of the valve, the user can evaluate the position of the valve relative to the patient's aortic annulus and may be able to determine whether the valve is functioning properly. If repositioning or removal is desired, with the buttons 46 positioned to engage the deployment actuator 21 with the threaded rod 36, the user may resheath the valve by rotating the deployment actuator in the direction opposite that used for deployment. Such rotation will cause the carriage assembly 40 to translate distally within the elongated space 34 in the housing 30 until the carriage assembly reaches the starting position shown in FIG. 1B, thereby re-collapsing the expanded part of the valve as the distal sheath 24 is moved distally over the compartment 23 and the partially deployed valve. With the valve resheathed, the user can reposition the delivery device 10 and commence the deployment procedure once again or simply remove the valve from the patient.

Once the proper positioning of the valve relative to the aortic annulus has been assured, the user may disengage the resheathing lock and complete the deployment process. The user can translate the carriage assembly 40 proximally to complete the deployment of the valve by rotating the deployment actuator 21. When the valve has been completely unsheathed, the stent portion of the valve self-expands and disengages from the retainer 25, thereby releasing the valve from the catheter assembly 16.

Figure 1D:
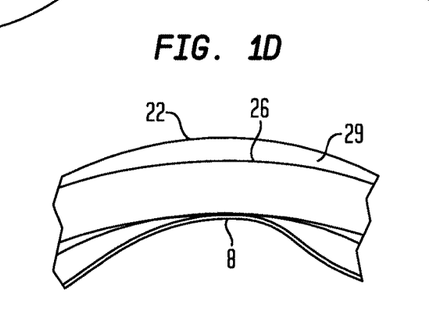
FIG. 1D is a longitudinal cross-section through a portion of the catheter assembly of FIG. 1C, shown within the vasculature of a patient.

The inventors have found that during operation of the delivery device 10 to deploy a prosthetic valve, the difference between the diameter of the outer surface of the inner shaft 26 and the inner surface of the outer shaft 22 (i.e., the lateral thickness of the space 29) can cause some potential problems during use of the delivery device. First, when the catheter assembly 16 bends around curves in the vasculature of a patient, there can be some relative axial movement between distal portions of the inner shaft 26 and distal portions of the outer shaft 22. For example, as shown in FIG. 1D, at locations in the vasculature 8 of a patient where the outer shaft 22 bends at a certain curvature (e.g., 120 degrees), the inner shaft 26 may contact the inside surface of the outer shaft closest to the bend in the vasculature, thereby permitting the inner shaft to have a less-sharp curvature (e.g., 140 degrees), taking up less axial length across the bent region compared to the outer shaft. As the outer shaft 22 begins to bend, the inner shaft 26 initially does not bend, but as the outer shaft continues to bend, the inner surface of the outer shaft will contact the inner shaft and cause it to bend to a lesser extent than the outer shaft, such that the inner shaft will contact the inside radius of the bend in the outer shaft.

Such a mismatch in bend curvatures may have a cumulative effect over multiple bends that results in an excess length in the inner shaft 26 that may twist or bind up within the outer shaft 22, or that may result in the atraumatic tip 14 moving distally relative to the distal sheath 24 due to the excess length of the inner shaft, opening up a gap between the distal end 27 of the distal sheath and the abutment surface 15 of the atraumatic tip (e.g., a gap of about 1 mm to about 15 mm). Having a gap between the distal end 27 of the distal sheath 24 and the proximally-facing abutment surface 15 of the atraumatic tip 14 is undesirable during movement of the catheter assembly 16 inside the native anatomy of a patient because native tissue may become lodged between the distal end of the distal sheath and the atraumatic tip, or may be abraded by the distal end of the distal sheath.

Such a gap between the distal end 27 of the distal sheath 24 and the abutment surface 15 of the atraumatic tip 14 may appear during insertion of the catheter assembly 16 into the patient, or it may appear after resheathing of the prosthetic valve during deployment. In some cases, the above-described mismatch in bend curvatures resulting in an excess length of the inner shaft 26 relative to the outer shaft 22 may result in no gap between the distal end 27 of the distal sheath 24 and the abutment surface 15 during insertion of the catheter assembly 16, because the excess length of the inner shaft may be temporarily taken up by twisting or binding of the inner shaft within the outer shaft 22.

During unsheathing of the prosthetic valve by moving the distal sheath 24 proximally relative to the inner shaft 26, the relative motion between the inner shaft and the outer shaft may relieve some of the twisting or binding of the inner shaft, thereby causing distal axial movement of distal portions of the inner shaft relative to distal portions of the outer shaft. Then, if it becomes necessary to resheath the valve during deployment, the user may be unable to completely close the compartment 23 due to the excess length of the inner shaft 26 relative to the outer shaft 22. That is, the distal sheath 24 may not be movable far enough for its distal end 27 to abut the proximally-facing abutment surface 15 of the atraumatic tip 14. To address this situation, one or more of the embodiments shown in FIGS. 2A and 2B and described below may be used to prevent or minimize the occurrence of such a gap between the distal end 27 of the distal sheath 24 and the abutment surface 15.

Figure 2A:
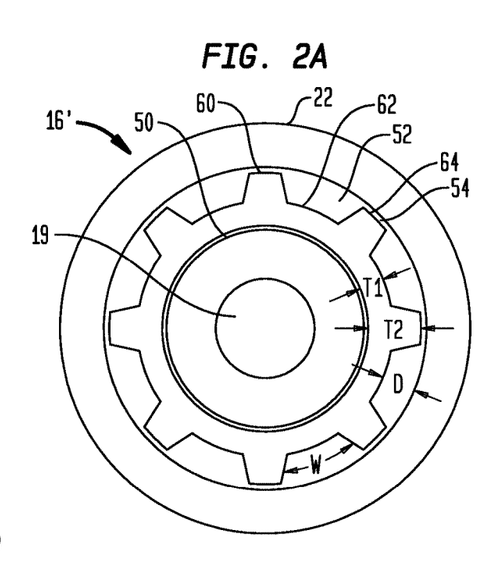
FIG. 2A is a lateral cross-section through a catheter assembly suitable for use with the delivery device of FIG. 1A, according to another embodiment.
Figure 2B:
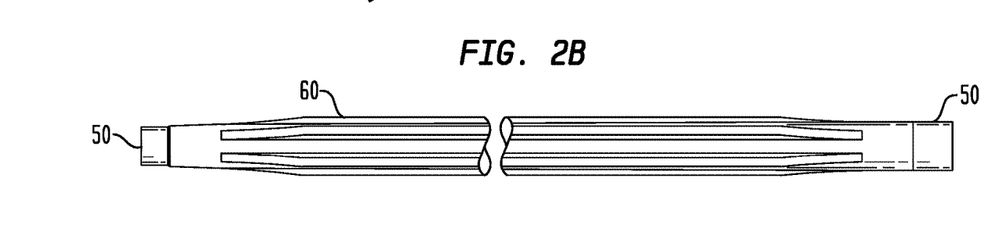
FIG. 2B is a side view of the spline tube in the catheter assembly of FIG. 2A.

Referring now to FIG. 2A, a catheter assembly 16' suitable for use with the delivery device 10 of FIGS. 1A and 1B is the same as the catheter assembly 16 described above, except that the inner shaft 26 is replaced with an inner shaft 50 radially surrounded by a spline tube 60. The lumen 19 of the inner shaft 50 may have the same diameter as that of the inner shaft 26, and the outer shaft 22 may be the same as the outer shaft 22 of FIGS. 1A-1C. However, the outer diameter of the inner shaft 50 may be smaller than the outer diameter of the inner shaft 26, so that there may be sufficient room between the inner shaft 50 and the outer shaft 22 to accommodate the spline tube 60. The inner shaft 50 may comprise or may consist essentially of a metal coil, made from 304B stainless steel, for example. The spline tube 60 may comprise or may consist essentially of a flexible material such as braided or extruded polyimide, polybutylene terephthalate (PBT), or polyetheretherketone (PEEK), for example.

The spline tube 60 may have a gear-shaped lateral cross-section with thinner portions 62 having a first thickness T1 in a radial direction and thicker portions 64 having a second thickness T2 in a radial direction. The thinner portions 62 and thicker portions 64 may alternate about the circumference of the spline tube 60, with the thicker portions 64 evenly spaced from one another in the circumferential direction. The thicker portions 64 may extend parallel to one another in a longitudinal direction of the spline tube 60. In some embodiments, at least part of the lengths of the thicker portions 64 may not extend parallel to one another in a longitudinal direction of the spline tube 60.

In other examples, the thicker portions 64 may extend at an oblique angle to the longitudinal direction of the spline tube 60. For example, one or more of the thicker portions 64 may extend in both a longitudinal direction and a circumferential direction in a spiral configuration about the longitudinal axis of the spline tube. In some examples, the thicker portions 64 may extend at a varying oblique angle to the longitudinal direction of the spline tube 60. For example, the thicker portions 64 may extend at a first oblique angle to the longitudinal direction of the spline tube 60 in a proximal region of the spline tube, and at a second oblique angle to the longitudinal direction of the spline tube in a distal region of the spline tube. The second oblique angle may be greater than or less than the first oblique angle. In some embodiments, the thicker portions 64 may be unevenly spaced from one another in the circumferential direction.

The thicker portions 64 may each extend continuously between opposite ends of the inner shaft 50, or one or more of the thicker portions may comprise a plurality of discontinuous segments each extending in the longitudinal direction of the spline tube 60. The thicker portions 64 may be an array of protrusions having the cross-sections shown in FIG. 2A, and the protrusions may each have any longitudinal side view shape, e.g., a cube or a rectangular prism, among others. Such protrusions may alternatively have a curved longitudinal side view profile, such as a cylinder, a cone, a frusto-conical shape, or an oblong curved shape, among others, but the cross-sections of such curved protrusions would vary depending on the position at which the cross-section is taken.

As shown in FIG. 2A, there may be eight thinner portions 62, and eight thicker portions 64, each thinner portion and each thicker portion extending by the same distance in the circumferential direction. In other examples, there may be any number of thinner portions 62 and thicker portions 64, and any or all of the thinner portions and/or thicker portions may extend over the same or different distances in the circumferential direction. Although the spline tube 60 is shown as being formed from a single unitary material (e.g., an extruded polymer), that need not be the case. In other examples, the spline tube may comprise any number of different materials affixed to one another. For example, the thicker portions 64 may be formed by affixing longitudinal strips of material to the outer surface of a thin cylindrical tube having a uniform thickness T1.

The spline tube 60 may have an outer diameter at the thicker portions 64 that is very close to the inner diameter of the outer shaft 22. In a preferred embodiment, the diametric clearance between the spline tube 60 at the thicker portions 64 and the outer shaft 22 may be about 0.001" to about 0.006"; that is, the difference between the outer diameter of the spline tube at the thicker portions may be about 0.001" to about 0.006" less than the inner diameter of the outer shaft 22. A diametric clearance of about 0.001" to about 0.006" forms gaps 54 between individual thicker portions 64 and the outer shaft 22 of half of the diametric clearance, or about 0.0005" to about 0.003" in a preferred embodiment. In comparison, the diametric clearance between the inner shaft 26 and the outer shaft 22 shown in FIG. 1C may be about 0.014", and the lateral thickness of the space 29 therebetween may be about 0.007".

The spline tube 60 and the outer shaft 22 may define channels 52, each channel radially disposed between a corresponding one of the thinner portions 62 and the inner surface of the outer shaft, and circumferentially disposed between two adjacent ones of the thicker portions 64. Adjacent ones of the channels 52 may be separated from one another by one of the thicker portions 64, or in some embodiments having discontinuous thicker portions, adjacent ones of the channels may connect to one another at one or more locations between the opposite ends of the inner shaft 50.

In a preferred embodiment, the diametric clearance between the thinner portions 62 of the spline tube 60 and the inner surface of the outer shaft 22 may be about 0.028", or about two times the diametric clearance between the inner shaft 26 and the outer shaft shown in FIG. 1C. Having a diametric clearance of about 0.028" corresponds to channels 52 having a depth D in a radial direction between individual thinner portions 62 and the outer shaft 22 of half of the diametric clearance, or about 0.014" in a preferred embodiment. As can be seen in FIG. 2A, each channel 52 may have an average width W in a circumferential direction between adjacent ones of the thicker portions 64 of about 0.28", or about equal to the diametric clearance between the thinner portions 62 and the inner surface of the outer shaft 22.

The depth D of the channels 52 in the catheter assembly 16' of FIG. 2A may provide less resistance to flow of a flushing liquid therethrough compared to the smaller thickness of the space 29 between the inner shaft 26 and the outer shaft 22 of FIG. 1C. Also, compared to the embodiment of FIG. 1C, the small gaps 54 between individual thicker portions 64 and the outer shaft 22 in the catheter assembly 16' of FIG. 2A may permit less relative axial movement between distal portions of the inner shaft 26 and distal portions of the outer shaft 22 when the catheter assembly bends around curves in the vasculature of a patient. That is, at locations in the vasculature 8 of a patient where the spline tube 60 bends and may contact the inside surface of the outer shaft 22 closest to the bend in the vasculature, the mismatch in bend curvatures between the spline tube and the outer shaft may be less than in the embodiment of FIG. 1C, thereby reducing the potential gap that may appear during valve deployment between the distal end 27 of the distal sheath 24 and the abutment surface 15 of the atraumatic tip 14.

In a preferred embodiment, the spline tube 60 may be affixed to the inner shaft 50 at each end of the spline tube, but not between the ends, such that as the catheter assembly 16' bends around the vasculature of a patient, portions of the spline tube may slightly rotate relative to the inner shaft. Alternatively, the spline tube 60 may be affixed to the inner shaft 50 continuously or at a plurality of discrete locations throughout the length of the spline tube, thereby resulting in a greater amount of stiffening of the inner shaft compared to an embodiment in which the spline tube is only affixed to the inner shaft at the proximal and distal ends of the spline tube. In embodiments in which the inner shaft 50 is fluid-permeable (e.g., when the inner shaft comprises a metal coil), affixing at least the ends of the spline tube 60 to the inner shaft may provide sealing of the inner shaft, which may prevent flushing liquid flowing through the channels 52 from migrating through the inner shaft and into its lumen 19. In some embodiments, the spline tube 60 may not be affixed to the inner shaft 50. In such embodiments in which the spline tube 60 is not affixed to the inner shaft 50, the spline tube 60 may be free to rotate relative to the inner shaft.

Although the embodiments herein have been described as reducing unwanted relative axial movement between distal portions of the inner shaft 26 and distal portions of the outer shaft 22 when the catheter assembly bends around curves in the vasculature of a patient and during resheathing of a prosthetic heart valve, any of the devices and methods described herein may also be incorporated into a delivery device for any other type of medical device that can be delivered into a patient in a compartment that is covered by a distal sheath similar to those described herein. For example, a collapsible stent may be deployed into a patient using any of the devices described herein, and any of the devices and methods described herein may also be used to reduce unwanted relative axial movement between distal portions of the inner shaft and distal portions of the outer shaft of such a delivery device.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

In summary, the disclosure herein describes multiple embodiments of a delivery device for a collapsible prosthetic heart valve. The delivery device may include an operating handle and a catheter assembly. The operating handle may have a housing and a carriage movable relative to the housing. The catheter assembly may include an inner shaft around which a compartment is defined, an outer shaft surrounding at least a portion of the inner shaft, a distal sheath fixedly connected to the outer shaft, and a spline tube surrounding at least a portion of the inner shaft. The inner shaft may be operatively connected to the housing. The compartment may be adapted to receive the valve in an assembled condition. The outer shaft may be fixedly connected to the carriage and movable relative to the inner shaft and the housing. The outer shaft may define a lumen therein having an inner surface.

The distal sheath may be movable between a closed condition covering the compartment and an open condition uncovering the compartment for deployment of the valve. At least a portion of the spline tube may be disposed in the lumen of the outer shaft. The spline tube may have first portions with a first maximum thickness in a radial direction of the inner shaft and second portions with a second maximum thickness in the radial direction, the second maximum thickness being greater than the first maximum thickness. The spline tube and the outer shaft may together define one or more channels each at least partially bounded by the inner surface of the outer shaft, one of the first portions, and two adjacent ones of the second portions, the one or more channels providing liquid communication between the operating handle and the compartment; and/or the second portions may extend parallel to one another in a longitudinal direction of the inner shaft transverse to the radial direction, and may be spaced apart from one another in a circumferential direction of the inner shaft; and/or at least part of the lengths of the second portions may not extend parallel to one another in a longitudinal direction of the inner shaft transverse to the radial direction; and/or the first portions and the second portions may alternate in a circumferential direction of the inner shaft, such that the spline tube has a gear-shaped transverse cross-section defined by the first portions and the second portions; and/or the second portions may be evenly spaced from one another about the inner shaft in the circumferential direction; and/or each of the second portions may extend continuously between proximal and distal ends of the inner shaft; and/or one or more of the second portions may comprise a plurality of discontinuous segments each extending in a longitudinal direction of the inner shaft; and/or one or more of the plurality of discontinuous segments may have a curved longitudinal side view profile; and/or a first minimum gap may be defined between the first portions and the inner surface of the outer shaft, and a second minimum gap may be defined between the second portions and the inner surface of the outer shaft, the first minimum gap being at least twice the second minimum gap; and/or the second portions of the spline tube and the inner surface of the outer shaft may define a diametric clearance of about 0.001" to 0.006"; and/or the inner shaft may comprise a metal coil, and the spline tube may be affixed to proximal and distal ends of the inner shaft, the spline tube preventing liquid communication between a lumen of the metal coil and the one or more channels; and/or the spline tube may consist essentially of an extruded polymer material.

Also described herein is a method of flushing a liquid into a compartment of a delivery device for implanting a medical device in a patient. The method may include providing the delivery device having a catheter assembly and an operating handle. The operating handle may have a housing and a carriage movable relative to the housing. The catheter assembly including an inner shaft around which a compartment for the medical device is defined, an outer shaft surrounding at least a portion of the inner shaft, a distal sheath fixedly connected to the outer shaft, and a spline tube surrounding at least a portion of the inner shaft. The distal sheath may be movable between a fully closed condition covering the compartment and an open condition uncovering the compartment. At least a portion of the spline tube may be disposed in the lumen of the outer shaft. The spline tube and the outer shaft together may define one or more channels providing liquid communication between the operating handle and the compartment.

The method may also include mounting the medical device in the compartment, sliding the distal sheath to cover the compartment and the medical device, and flushing the liquid from the operating handle to the compartment through the one or more channels. The spline tube may have first portions having a first maximum thickness in a radial direction of the inner shaft and second portions having a second maximum thickness in the radial direction, the second maximum thickness being greater than the first maximum thickness. The one or more channels may each be at least partially bounded by the inner surface of the outer shaft, one of the first portions, and two adjacent ones of the second portions; and/or the second portions may extend parallel to one another in a longitudinal direction of the inner shaft transverse to the radial direction, and may be spaced apart from one another in a circumferential direction of the inner shaft; and/or the first portions and the second portions may alternate in a circumferential direction of the inner shaft, such that the spline tube has a gear-shaped transverse cross-section defined by the first portions and the second portions; and/or the second portions may be evenly spaced from one another about the inner shaft in the circumferential direction; and/or each of the second portions may extend continuously between proximal and distal ends of the inner shaft; and/or one or more of the second portions may comprise a plurality of discontinuous segments each extending in a longitudinal direction of the inner shaft; and/or a first minimum gap may be defined between the first portions and the inner surface of the outer shaft, and a second minimum gap may be defined between the second portions and the inner surface of the outer shaft, the first minimum gap being at least twice the second minimum gap; and/or the second portions of the spline tube and the inner surface of the outer shaft may define a diametric clearance of about 0.001" to 0.006"; and/or the inner shaft may comprise a metal coil, and the spline tube may be affixed to proximal and distal ends of the inner shaft, the spline tube preventing liquid communication between a lumen of the metal coil and the one or more channels during the flushing step; and/or the spline tube may consist essentially of an extruded polymer material.

The invention claimed is:

1. A delivery device for a collapsible prosthetic heart valve, the delivery device comprising:
    an operating handle having a housing and a carriage movable relative to the housing; and
    a catheter assembly, including:
        an inner shaft around which a compartment is defined, the inner shaft being operatively connected to the housing, the compartment being adapted to receive the valve in an assembled condition;
        an outer shaft surrounding at least a portion of the inner shaft, the outer shaft being fixedly connected to the carriage and movable relative to the inner shaft and the housing, the outer shaft defining a lumen therein having an inner surface;
        a distal sheath fixedly connected to the outer shaft, the distal sheath being movable between a closed condition covering the compartment and an open condition uncovering the compartment for deployment of the valve; and
        a spline tube surrounding at least a portion of the inner shaft, at least a portion of the spline tube disposed in the lumen of the outer shaft, the spline tube having first portions with a first maximum thickness in a radial direction of the inner shaft and second portions with a second maximum thickness in the radial direction, the second maximum thickness being greater than the first maximum thickness, each of the second portions extending continuously between proximal and distal ends of the inner shaft,
    wherein the spline tube and the outer shaft together define one or more channels each at least partially bounded by the inner surface of the outer shaft, one of the first portions, and two adjacent ones of the second portions, the one or more channels providing liquid communication between the operating handle and the compartment.

2. The delivery device of claim 1, wherein the second portions extend parallel to one another in a longitudinal direction of the inner shaft transverse to the radial direction, and are spaced apart from one another in a circumferential direction of the inner shaft.

3. The delivery device of claim 1, wherein the first portions and the second portions alternate in a circumferential direction of the inner shaft, such that the spline tube has a gear-shaped transverse cross-section defined by the first portions and the second portions.

4. The delivery device of claim 3, wherein the second portions are evenly spaced from one another about the inner shaft in the circumferential direction.

5. The delivery device of claim 1, wherein a first minimum gap is defined between the first portions and the inner surface of the outer shaft, and a second minimum gap is defined between the second portions and the inner surface of the outer shaft, the first minimum gap being at least twice the second minimum gap.

6. The delivery device of claim 1, wherein the second portions of the spline tube and the inner surface of the outer shaft define a diametric clearance of about 0.001" to 0.006".

7. The delivery device of claim 1, wherein the inner shaft comprises a metal coil, and the spline tube is affixed to proximal and distal ends of the inner shaft, the spline tube preventing liquid communication between a lumen of the metal coil and the one or more channels.

8. The delivery device of claim 1, wherein the spline tube consists essentially of an extruded polymer material.

9. A delivery device for a collapsible prosthetic heart valve, the delivery device comprising:
    an operating handle having a housing and a carriage movable relative to the housing; and
    a catheter assembly, including:
        an inner shaft around which a compartment is defined, the inner shaft being operatively connected to the housing, the compartment being adapted to receive the valve in an assembled condition:
        an outer shaft surrounding at least a portion of the inner shaft, the outer shaft being fixedly connected to the carriage and movable relative to the inner shaft and the housing, the outer shaft defining a lumen therein having an inner surface;
        a distal sheath fixedly connected to the outer shaft, the distal sheath being movable between a closed condition covering the compartment and an open condition uncovering the compartment for deployment of the valve; and
        a spline tube surrounding at least a portion of the inner shaft, at least a portion of the spline tube disposed in the lumen of the outer shaft, the spline tube having first portions with a first maximum thickness in a radial direction of the inner shaft and second portions with a second maximum thickness in the radial direction, the second maximum thickness being greater than the first maximum thickness,
    wherein the spline tube and the outer shaft together define one or more channels each at least partially bounded by the inner surface of the outer shaft, one of the first portions, and two adjacent ones of the second portions, the one or more channels providing liquid communication between the operating handle and the compartment,
    wherein one or more of the second portions comprises a plurality of discontinuous segments each extending in a longitudinal direction of the inner shaft.

10. The delivery device of claim 9, wherein at least part of the lengths of the second portions do not extend parallel to one another in a longitudinal direction of the inner shaft transverse to the radial direction.

11. The delivery device of claim 9, wherein one or more of the plurality of discontinuous segments has a curved longitudinal side view profile.

12. A method of flushing a liquid into a compartment of a delivery device for implanting a medical device in a patient, the method comprising:
providing a delivery device having a catheter assembly and an operating handle, the operating handle having a housing and a carriage movable relative to the housing, the catheter assembly including an inner shaft around which a compartment for the medical device is defined, an outer shaft surrounding at least a portion of the inner shaft, a distal sheath fixedly connected to the outer shaft, the distal sheath being movable between a fully closed condition covering the compartment and an open condition uncovering the compartment, and a spline tube surrounding at least a portion of the inner shaft, at least a portion of the spline tube being disposed in the lumen of the outer shaft, the spline tube and the outer shaft together defining one or more channels providing liquid communication between the operating handle and the compartment;
mounting the medical device in the compartment;
sliding the distal sheath to cover the compartment and the medical device; and
flushing the liquid from the operating handle to the compartment through the one or more channels,
wherein the spline tube has first portions having a first maximum thickness in a radial direction of the inner shaft and second portions having a second maximum thickness in the radial direction, the second maximum thickness being greater than the first maximum thickness, and the one or more channels are each at least partially bounded by the inner surface of the outer shaft, one of the first portions, and two adjacent ones of the second portions, each of the second portions extending continuously between proximal and distal ends of the inner shaft.

13. The method of claim 12, wherein the second portions extend parallel to one another in a longitudinal direction of the inner shaft transverse to the radial direction, and are spaced apart from one another in a circumferential direction of the inner shaft.

14. The method of claim 12, wherein the first portions and the second portions alternate in a circumferential direction of the inner shaft, such that the spline tube has a gear-shaped transverse cross-section defined by the first portions and the second portions.

15. The method of claim 14, wherein the second portions are evenly spaced from one another about the inner shaft in the circumferential direction.

16. The method of claim 12, wherein a first minimum gap is defined between the first portions and the inner surface of the outer shaft, and a second minimum gap is defined between the second portions and the inner surface of the outer shaft, the first minimum gap being at least twice the second minimum gap.

17. The method of claim 12, wherein the inner shaft comprises a metal coil, and the spline tube is affixed to proximal and distal ends of the inner shaft, the spline tube preventing liquid communication between a lumen of the metal coil and the one or more channels during the flushing step.

* * * * *